United States Patent
Ganssle et al.

(10) Patent No.: US 11,143,014 B2
(45) Date of Patent: Oct. 12, 2021

(54) NUCLEAR MAGNETIC RESONANCE SENSORS EMBEDDED IN CEMENT

(71) Applicant: Halliburton Energy Services, Inc., Houston, TX (US)

(72) Inventors: Paul Joseph Ganssle, Houston, TX (US); Krishna M. Ravi, Kingwood, TX (US); Songhua Chen, Katy, TX (US); Peter James Boul, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 354 days.

(21) Appl. No.: 15/116,412

(22) PCT Filed: May 19, 2014

(86) PCT No.: PCT/US2014/038620
§ 371 (c)(1),
(2) Date: Aug. 3, 2016

(87) PCT Pub. No.: WO2015/178883
PCT Pub. Date: Nov. 26, 2015

(65) Prior Publication Data
US 2017/0218748 A1    Aug. 3, 2017

(51) Int. Cl.
*E21B 47/005* (2012.01)
*E21B 47/135* (2012.01)
(Continued)

(52) U.S. Cl.
CPC ............ *E21B 47/005* (2020.05); *E21B 33/14* (2013.01); *E21B 47/135* (2020.05); *G01N 24/08* (2013.01);
(Continued)

(58) Field of Classification Search
CPC .... E21B 47/0005; E21B 33/14; E21B 47/123; G01N 24/08; G01N 33/383
See application file for complete search history.

(56) References Cited

U.S. PATENT DOCUMENTS 5,167,983 A * 12/1992 Liu .................. G01R 33/34007
427/105
5,610,331 A * 3/1997 Georgi .................... E21B 47/10
73/152.18
(Continued)

FOREIGN PATENT DOCUMENTS

GB      2534484 A     7/2016
WO   WO-2015178883 A1   11/2015

OTHER PUBLICATIONS

Valori, A., et al., "The morphology of C—S—H: Lessons from $^1$H nuclear magnetic resonance relaxometry", *Cement and Concrete Research*, 49, (2013), 65-81.

(Continued)

*Primary Examiner* — Waseem Moorad
*Assistant Examiner* — Neel Girish Patel
(74) *Attorney, Agent, or Firm* — Chamberlain Hrdlicka

(57) ABSTRACT

Various embodiments include nuclear magnetic resonance (MR) sensor array systems and methods are disclosed. One such system includes a downhole casing having at least one MR sensor array peripherally coupled to an outside of the casing. At least one MR sensor array can include an MR sensor configured to monitor a cement/fluid mix composition while the cement is setting.

22 Claims, 9 Drawing Sheets

(51) Int. Cl.
  *E21B 33/14*   (2006.01)
  *G01N 24/08*   (2006.01)
  *G01R 33/38*   (2006.01)
  *G01N 33/38*   (2006.01)

(52) U.S. Cl.
  CPC ....... *G01N 33/383* (2013.01); *G01R 33/3808* (2013.01)

(56) References Cited

U.S. PATENT DOCUMENTS

| | | | |
|---|---|---|---|
| 6,279,392 B1* | 8/2001 | Shahin, Jr. | C09K 8/42 73/152.52 |
| 6,378,627 B1* | 4/2002 | Tubel | E21B 4/18 175/24 |
| 7,543,512 B2* | 6/2009 | Smith | E21B 47/01 73/865.8 |
| 7,975,541 B2* | 7/2011 | Large | E21B 47/0002 166/241.5 |
| 8,461,836 B2* | 6/2013 | Blank | G01N 24/08 324/303 |
| 9,181,759 B1* | 11/2015 | Yusuf | E21B 17/1021 |
| 9,243,489 B2* | 1/2016 | Veeningen | E21B 47/02 |
| 9,678,239 B2* | 6/2017 | Habashy | G01V 3/20 |
| 9,885,805 B2* | 2/2018 | Hayman | E21B 47/00 |
| 2002/0000808 A1 | 1/2002 | Nichols | |
| 2003/0117134 A1 | 6/2003 | Almaguer | |
| 2003/0192695 A1* | 10/2003 | Dillenbeck | E21B 33/05 166/285 |
| 2005/0017723 A1* | 1/2005 | Entov | E21B 43/26 324/346 |
| 2006/0005965 A1* | 1/2006 | Chouzenoux | E21B 47/0006 166/250.11 |
| 2007/0206555 A1 | 9/2007 | Kruspe et al. | |
| 2009/0020283 A1* | 1/2009 | Manin | E21B 47/122 166/147 |
| 2009/0218097 A1* | 9/2009 | Cook | E21B 37/00 166/250.17 |
| 2012/0131996 A1* | 5/2012 | Anish | E21B 17/1021 73/152.54 |
| 2012/0241172 A1* | 9/2012 | Ludwig | E21B 47/01 166/382 |
| 2013/0269931 A1* | 10/2013 | Badri | E21B 49/00 166/250.01 |
| 2014/0009148 A1* | 1/2014 | Walsh | G01V 3/14 324/303 |
| 2014/0062487 A1* | 3/2014 | Bloemenkamp | G01V 3/24 324/324 |
| 2014/0102792 A1* | 4/2014 | Lachner, Jr. | E21B 7/002 175/40 |
| 2014/0347056 A1* | 11/2014 | Hayman | E21B 47/00 324/355 |
| 2016/0033664 A1* | 2/2016 | Cheng | E21B 47/00 73/152.57 |
| 2016/0084062 A1* | 3/2016 | Negre | E21B 47/12 166/250.01 |
| 2016/0258269 A1* | 9/2016 | Musso | E21B 47/0005 |
| 2017/0115426 A1* | 4/2017 | Martin | G01V 3/26 |
| 2018/0003027 A1* | 1/2018 | Donzier | E21B 47/00 |
| 2018/0003850 A1* | 1/2018 | Jaaskelainen | G01V 3/38 |
| 2018/0245450 A1* | 8/2018 | Stokes | E21B 29/02 |

OTHER PUBLICATIONS

"International Application Serial No. PCT/US2014/038620, International Search Report dated Feb. 6, 2015", 4 pgs.
"International Application Serial No. PCT/US2014/038620, Written Opinion dated Feb. 6, 2015", 11 pgs.
"Venezuela Application Serial No. 2015-000450, Office Action dated Jun. 13, 2016".

* cited by examiner

NUCLEAR MAGNETIC RESONANCE SENSORS EMBEDDED IN CEMENT

PRIORITY APPLICATION

This application is a U.S. National Stage Filing under 35 U.S.C. 371 from International Application No. PCT/US2014/038620, filed on May 19, 2014 and published as WO 2015/178883 A1 on Nov. 26, 2015, which applications and publication are incorporated herein by reference in their entirety.

BACKGROUND

In drilling wells for oil and gas exploration, a drilling engineer, usually with input from geologists and others, can choose strategic depths at which the hole will need to be cased in order for drilling to reach a desired depth. This decision is often based on subsurface data such as formation pressures, strengths, and makeup.

A casing is a relatively large diameter pipe that is assembled and inserted into a recently drilled section of a borehole and typically held into place with cement. It is desirable to detect flaws or contamination in the cement in order to reduce the possibility of the casing not being held securely in place.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Figure 1:
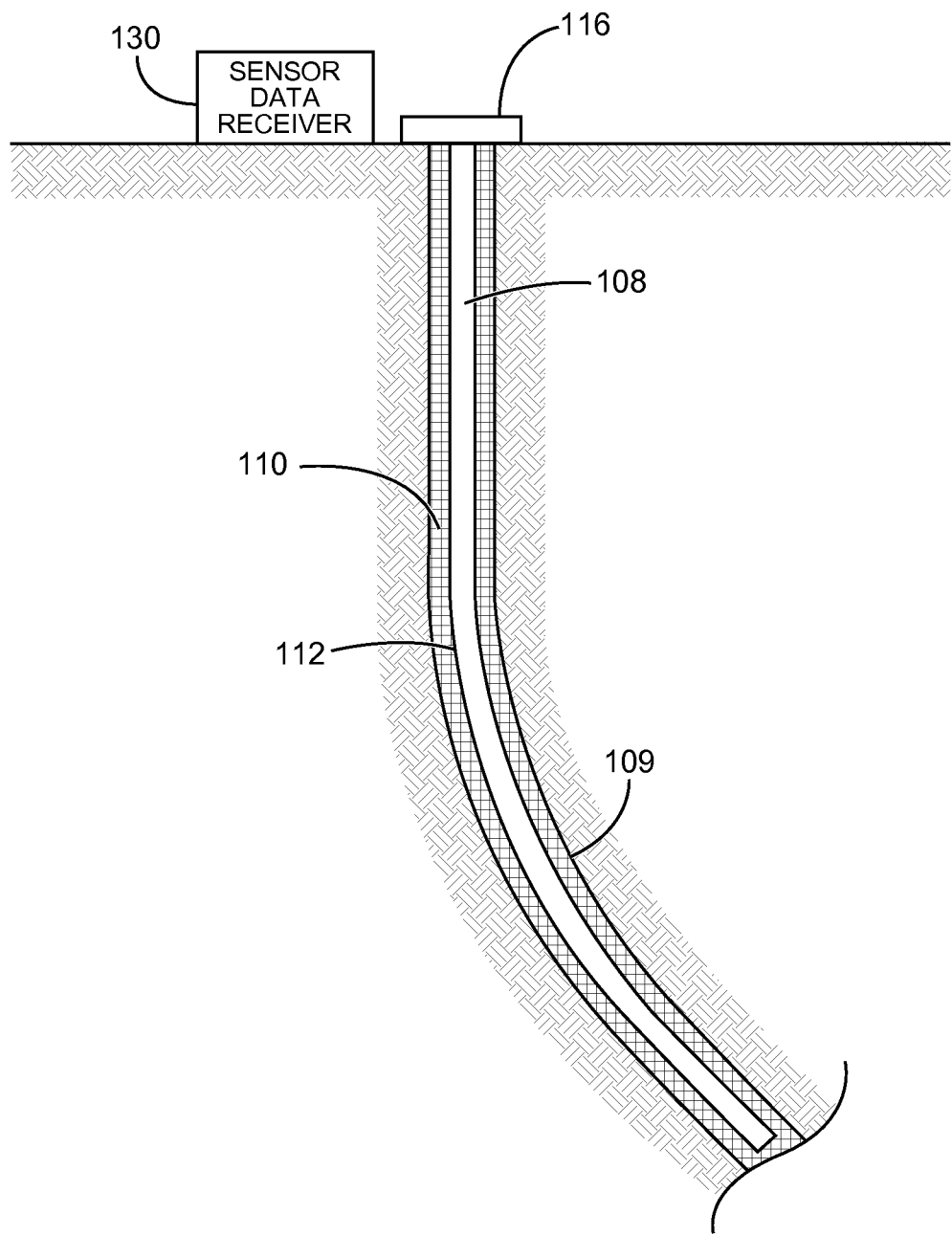
FIG. 1 shows diagram of an embodiment of a wellbore having a casing with attached sensors.

FIG. 1 is a diagram of an embodiment of a wellbore installation to measure, monitor, and or remove fluids in a subterranean formation. The wellbore 108 comprises an elongated cylindrical borehole 109 drilled through a geological formation and lined with a metallic casing 112 that extends substantially continuously in the borehole 109 for a predetermined depth. The casing 112 forms a hollow cylindrical conduit along which production fluid (e.g., a mixture of liquid and vapor) can be conducted to a wellhead 116 at the Earth's surface.

An annular space between the production casing 112 and a substantially cylindrical wall of the borehole 109 may be filled with an impervious material 110 (e.g., cement) for at least some portions of the length of the wellbore 108. The cement 110 reduces the inflow of liquids radially into the fluid conduit provided by the wellbore 108 in such backfilled portions as well as holds the casing 112 in place. Other portions of the wellbore 108, along its length, may be specifically configured to be permeable to radial movement of hydrocarbons from the geological formation into the wellbore 108, thus forming a plurality of production zones spaced along the length of the wellbore 108. In some instances, the wellbore 108 does not necessarily comprise production zones that are segregated by such structural components of the wellbore 108, but naturally occurring production zones may nevertheless exist because of variations in geological formations through which the wellbore 108 extends.

While injecting the cement into the space between the casing 112 and the geological formation, contaminants such as mud or geological fluids can contaminate the cement. Such contaminates can result in flawed and/or structurally deficient cement. Thus, it is desirable to monitor the cement as it is injected and as it cures. The present embodiments use low magnetic field, magnetic resonance (MR) sensors (including nuclear magnetic resonance (NMR) sensors) attached to the casing 112 and embedded in the cement in order to perform this monitoring. The sensor data can then be transmitted to a sensor data receiver 130 at the surface in order to process the data and determine the quality of the cement as it is setting. The sensor can be powered by a battery or battery pack or by an external power source transmitted to the sensor along the outside of the casing via a wired connection or through a fiber optic line.

NMR sensors can be used as a tool for probing the microenvironments in heterogeneous media, such as cements. The NMR sensors provide the ability to extract information such as porosity, pore size distribution, permeability, viscosity, and chemical composition. The NMR sensor can monitor any correlates to cement quality and/or contamination level. Since the sensors are both stationary and in direct contact with the sample can significantly reduce the complexity of making relatively high signal-to-noise ratio (SNR) measurements as compared to current wireline and measurement while drilling (MWD) NMR tools.

NMR can occur when the medium is subjected to a static magnetic field, $B_0$, and to an oscillating magnetic field, $B_1$. When subjected to the applied static magnetic field, polarization of nuclear magnetic spins of the medium occurs based on a spin number of the medium and a magnetic field strength. Applying an electromagnetic field to the medium in the static magnetic field can perturb the polarization established by the static magnetic field. In optimal measurements, the static magnetic field and the perturbing field are perpendicular to each other. Collected responses received from the medium related to the total magnetization of nuclear spins in the medium, in response to these applied fields, can be used to investigate properties of the medium and may provide imaging of the medium. It is noted that magnetization is proportional to polarization.

NMR measurements can be created by the oscillation of excited nuclear magnetic spins in the transverse plane. The transverse plane is the direction perpendicular to the magnetic field. This oscillation eventually dies out and the equilibrium magnetization returns. The return process is referred to as longitudinal relaxation. The time constant, $T_1$, for nuclei to return to their equilibrium magnetization, $M_0$, is typically referred to as the longitudinal relaxation time or the spin lattice relaxation time. The magnetization dephasing, that is losing coherence along the transverse plane, is given by the time constant $T_2$ and is typically referred to as the spin-spin relaxation time. The loss of phase coherence can be caused by several factors including interactions between spins or magnetic gradients.

The NMR sensors can include any design that can be implemented in an NMR system. For example, in situ and ex situ are two such sensors.

Figure 2:
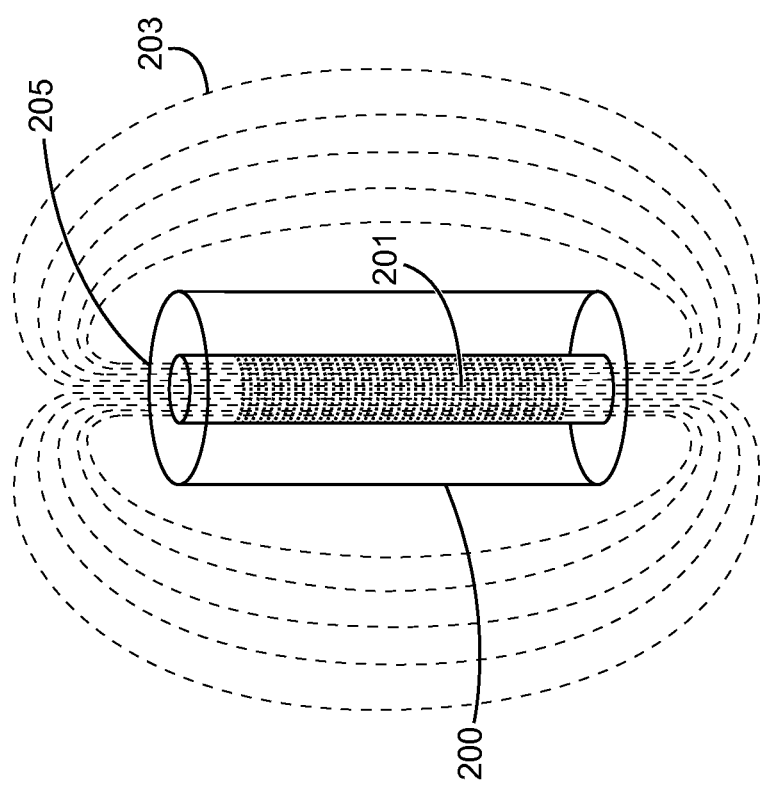
FIG. 2 shows diagram of an embodiment of a nuclear magnetic resonance (NMR) in-situ sensor design.

FIG. 2 illustrates a diagram of an in situ NMR sensor. In such a sensor, the measurements can provide relatively larger SNR as compared to the ex situ sensor since the measurements are made on cement that has perfused into the bore of the magnet. The in situ sensor measurements are made in a homogeneous field that can increase the transceiver coil's filling factor as well as enable high-resolution chemical spectroscopy to be performed.

The in situ sensor of FIG. 2 shows a permanent magnet 200 having a coil 201 wrapped around a hollow core of the magnet. The magnetic field 203 is formed through the core and around the magnet.

Since the in situ sensor includes a hollow core, measurements can be made of the cement sample inside the homogeneous center 205 of the magnetic field. 203.

Figure 3:
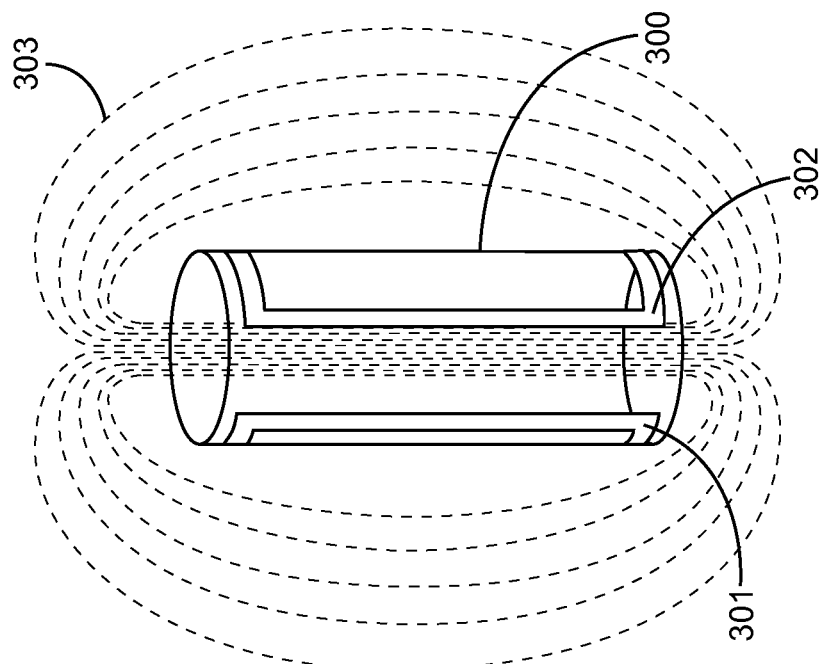
FIG. 3 shows a diagram of an embodiment of an NMR ex-situ sensor design.

FIG. 3 illustrates a diagram of an ex situ NMR sensor. This sensor includes the coils 301, 302 around the exterior of a permanent magnet 300. The magnetic field 303 is centered at the core of the magnet 300 but, not having a hollow core, the NMR measurements are performed in the fringe field of the permanent magnet. The signal comes from a resonant shell at a radius of investigation determined by the field gradient and measurement frequency.

While the SNR of the ex situ sensor can be lower than the in situ, measurements can be made at a greater distance from the tool as compared to an in situ sensor. Also, since the omnipresent field gradient makes it possible to make measurements of the radial profile of the NMR signal, it is relatively simple to make NMR diffusion measurements.

In either the in situ or the ex situ sensors, the sensor can protrude from the casing to measure a greater amount of the cement. This can be accomplished using one relatively large sensor or a plurality of relatively smaller sensors (e.g., array of sensors).

One relatively large sensor can provide a simpler design and can have a greater SNR than an array of smaller sensors. However, the array of sensors can provide a greater spatial resolution and enable a design that rejects common-mode noise. Depending on the cost and the field profile, the array of sensors can be located around a single larger magnet or a plurality of smaller, individual-sized magnets.

FIGS. 4-7 illustrate various embodiments of an array of sensors. These embodiments are for purposes of illustration only as an array of NMR sensors can include one or more NMR sensors and can take any configuration. Additionally, the NMR sensors can be in situ, ex situ, or some other sensor design.

Figure 4:
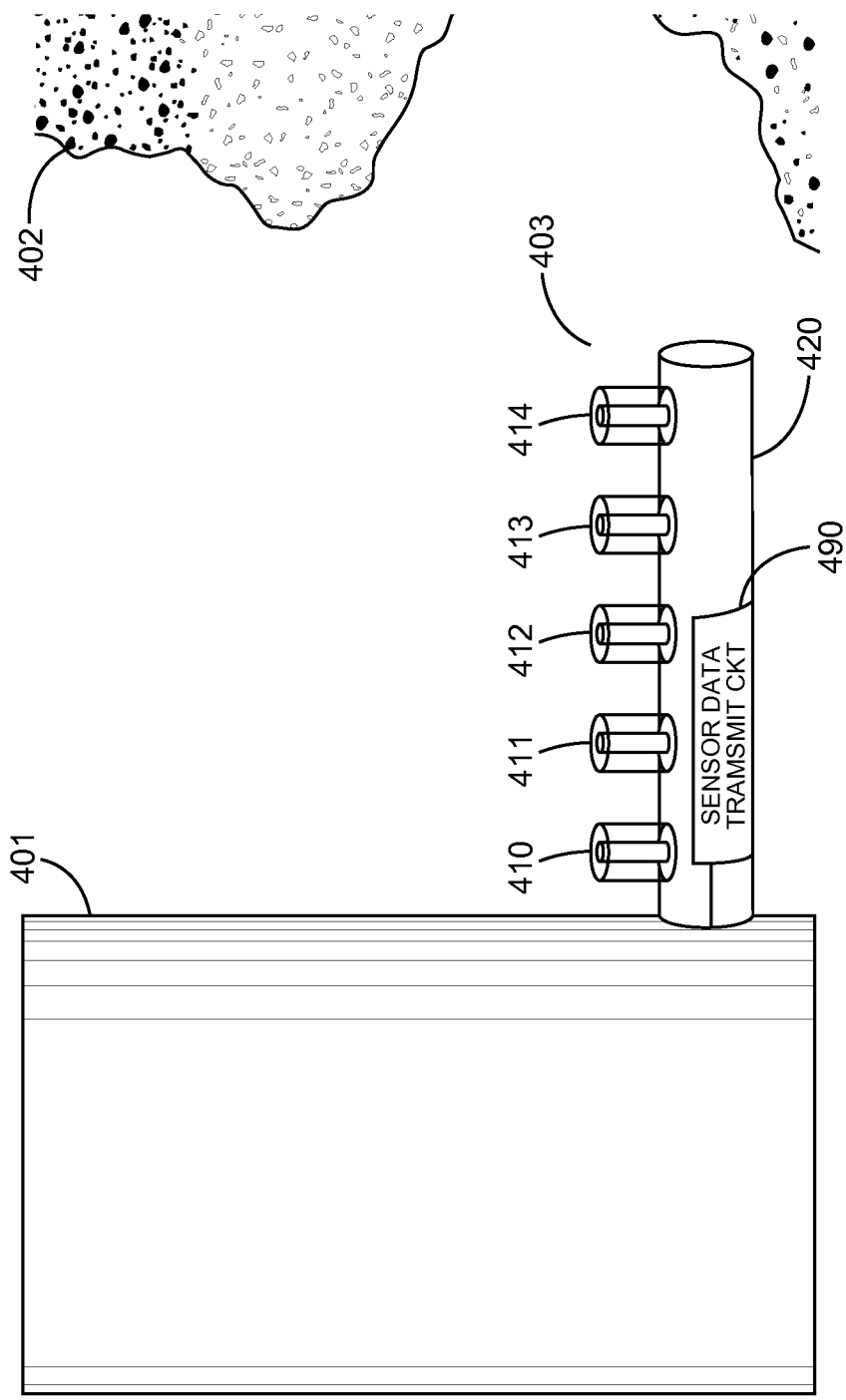
FIG. 4 shows a diagram of an embodiment of a casing having an attached NMR sensor.

The embodiment of FIG. 4 includes a casing 401 located within a geological formation 402. The sensor array 403 includes a single NMR in situ sensor 420 having a plurality of permanent magnets 410-416. The coil (not shown) is located within the sensor 420. The hollow core of each of the permanent magnets 410-416 enables the cement/fluid mixture to enter the core for analysis. The sensor data transmission circuit 490 for reading the sensor data and transmitting the sensor data to the surface can be located within the sensor housing 420, built in a container adjacent to the casing 401, or attached to the sensor 420 in some other location. The signal containing the cement/fluid mixture sensor data can be transmitted directly to the surface wirelessly, through a wireline logging tool, or with a conductor.

Figure 5:
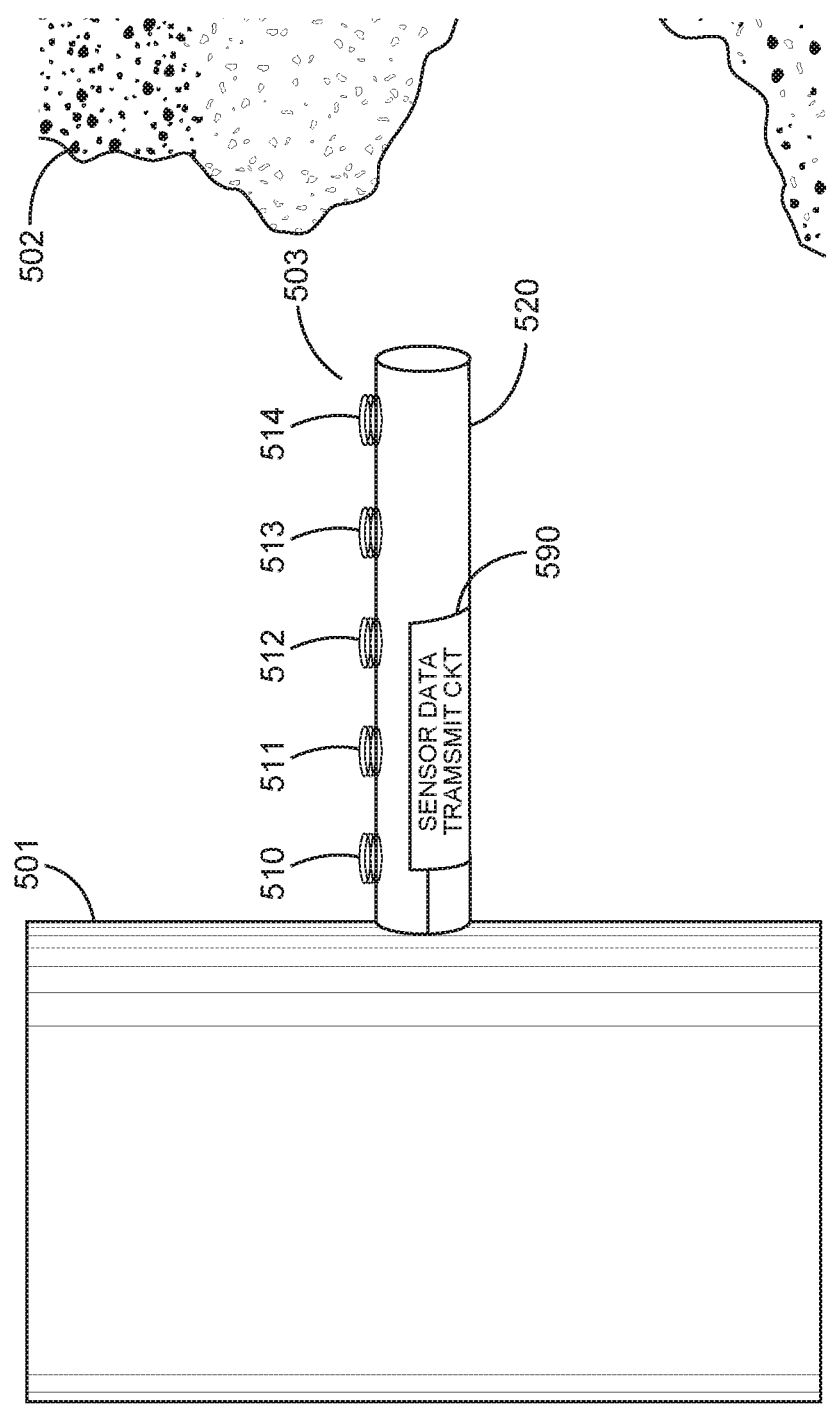
FIG. 5 shows a diagram of another embodiment of a casing having an attached NMR sensor.

The embodiment of FIG. 5 includes a casing 501 located within a geological formation 502. The sensor array 503 includes a plurality of ex situ sensors 510-514 on a single magnet 520. The plurality of ex situ sensors 510-514 each include the coils. The sensor data transmission circuit 590 for reading the sensor data and transmitting the sensor data to the surface can be located within the magnet housing 520, built in a container adjacent to the casing 501, or attached to the magnet housing 520 in some other location. The signal containing the cement/fluid mixture sensor data can be transmitted directly to the surface wirelessly, through a wireline logging tool, or through a conductor.

Figure 6:
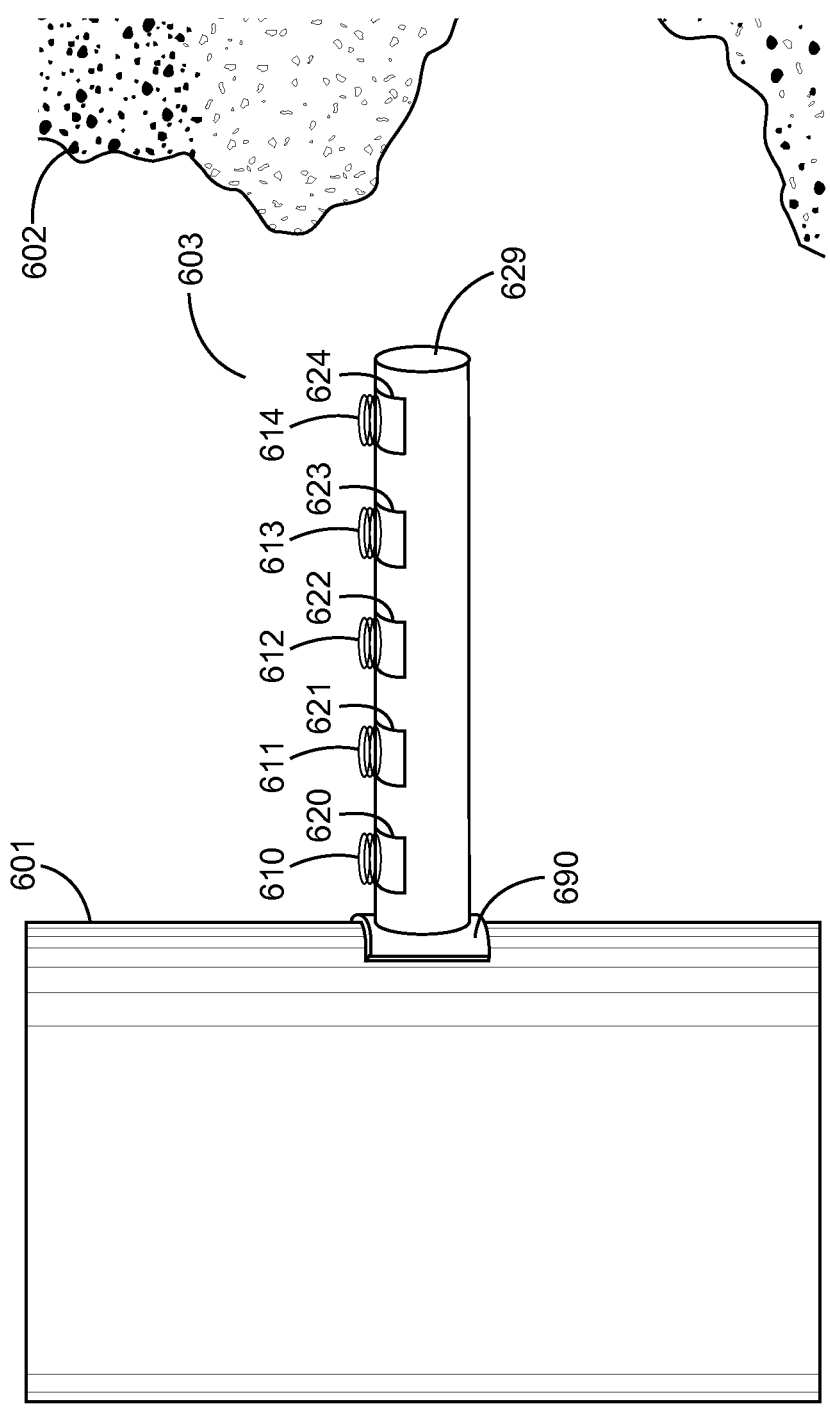
FIG. 6 shows a diagram of another embodiment of a casing having an attached NMR sensor.

The embodiment of FIG. 6 includes a casing 601 located within a geological formation 602. The sensor array 603 includes a plurality of ex situ sensors 610-614 each on their respective individual magnet 620-624. The support 629 can include the sensor data transmission circuit 690 for reading the sensor data and transmitting the sensor data to the surface. The transmission circuit 690 can also be built into a container adjacent to the casing 601, as shown, or attached to the support 629 in some other location. The signal containing the cement/fluid mixture sensor data can then be transmitted directly to the surface wirelessly, through a wireline logging tool, or through a conductor.

Figure 7:
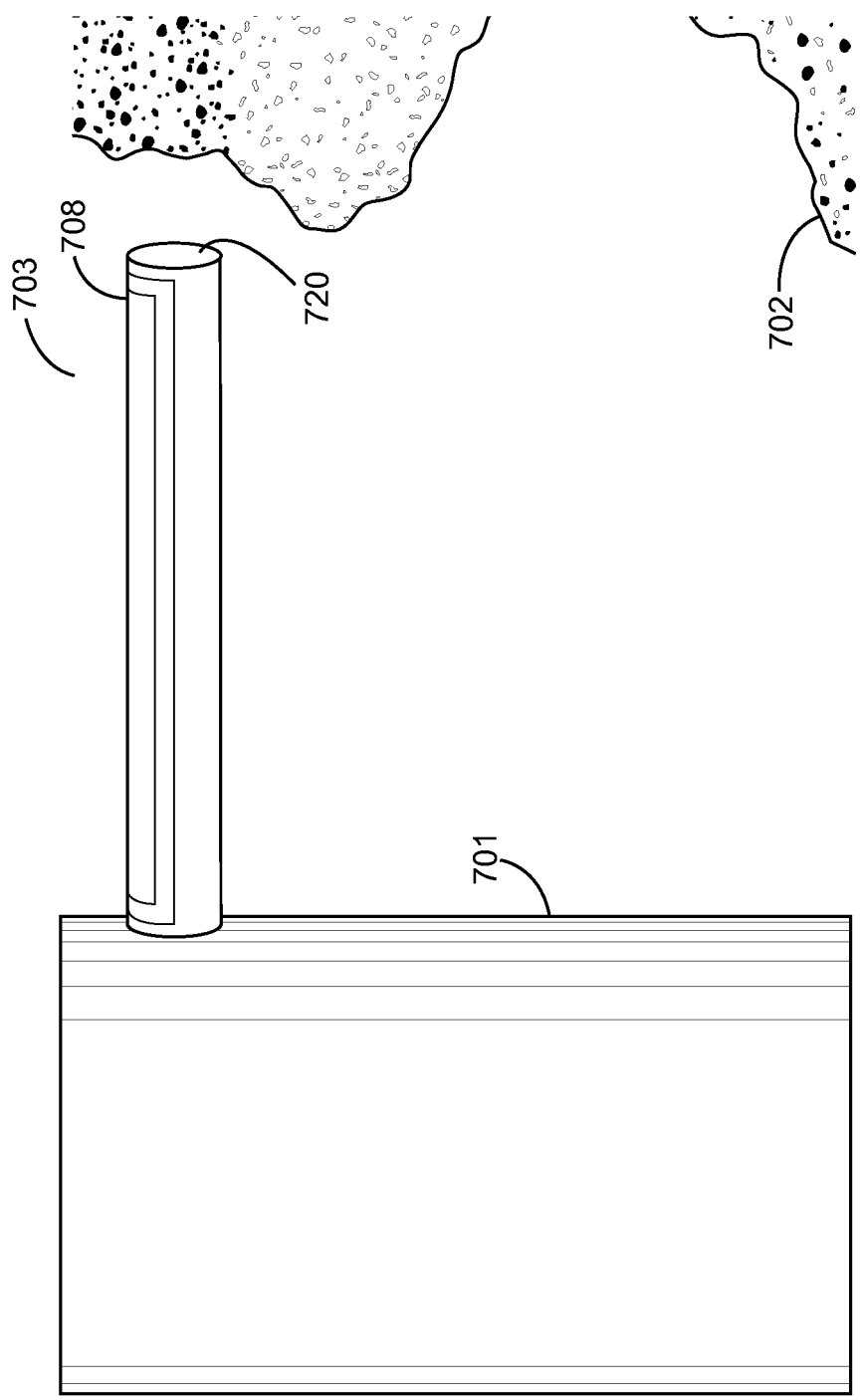
FIG. 7 shows a diagram of another embodiment of a casing having an attached NMR sensor.

The embodiment of FIG. 7 includes a casing 701 located within a geological formation 702. The ex situ sensor array 703 includes a single magnet 720 having a single coil 708. The electronics (not shown) for reading the sensor data can be located within the magnet housing 720, built in a container adjacent to the casing 701, or attached to the magnet housing 720 in some other location. The signal containing the cement/fluid mixture analysis of the sensor data can then be transmitted directly to the surface wirelessly or through a wireline logging tool.

Figure 8:
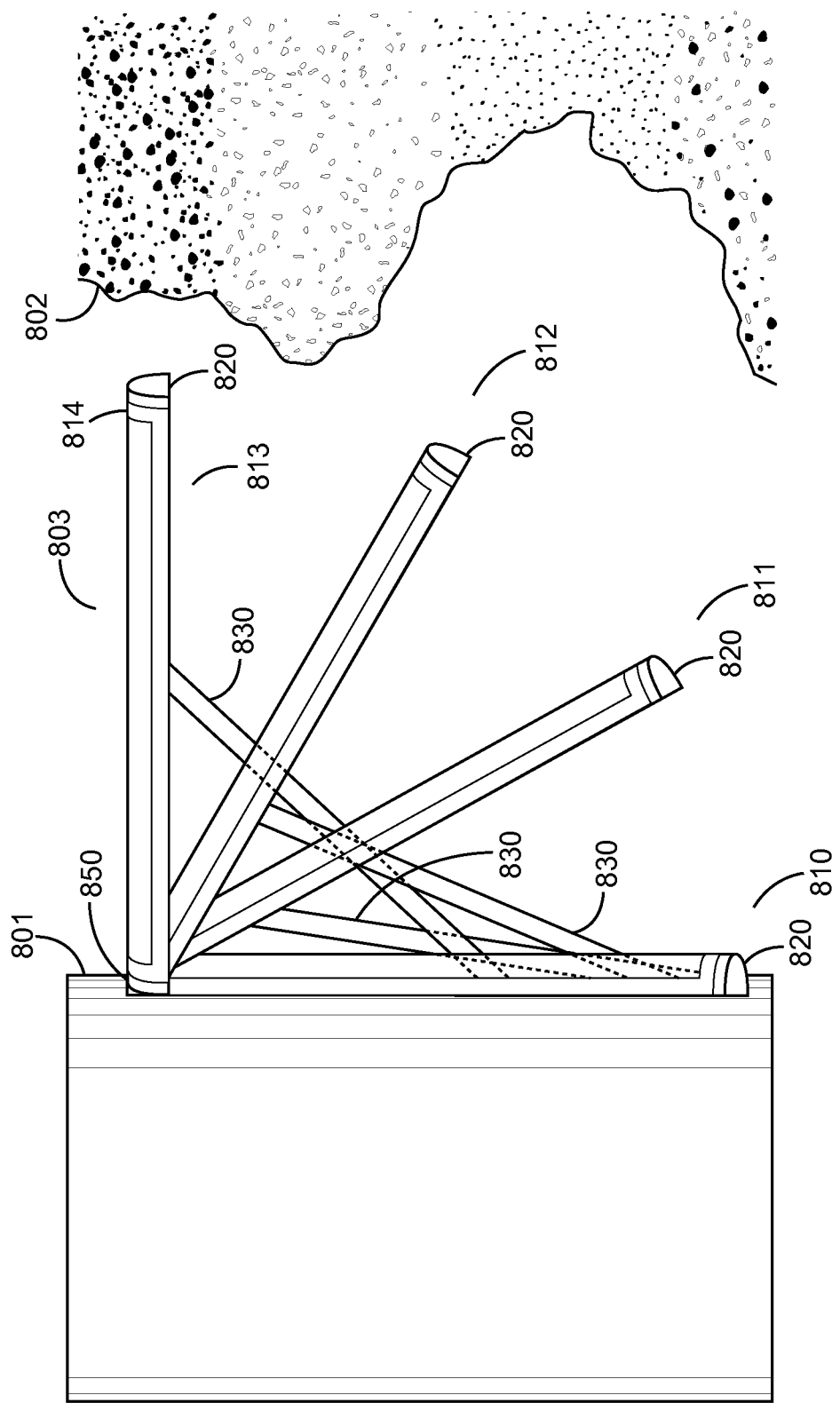
FIG. 8 shows a diagram of an embodiment of a casing having an expanding NMR sensor.

FIG. 8 illustrates an expanding sensor array 803. The sensor array 803 of the embodiment of FIG. 8 shows only a single sensor coil 814 on a single magnet 820. However, other embodiments can include any of the embodiments of FIGS. 4-7 (either ex situ or in situ) in an expanding sensor array as illustrated in FIG. 8. Such an expanding array would provide a compact arrangement while the casing 801 is being lowered into the geological formation 802 and then expand after the casing has been built.

The various stages of expansion 810-813 are shown in FIG. 8. An initial compact stage 810 is illustrated as the magnet 820 being held to the casing 801. Once the casing 801 is in place, a command can be sent to a latch (not shown) that unlatches and enables a hinge 850 and support 830 to push the magnet 820 away from the casing 801. The hinge 850 and support 830 enables the sensor array 803 to expand as far as the geological formation 802 allows. For example, the magnet 820 with the sensor array 803 can stop at any one of the illustrated locations of expansion 810-813. The support 830 would then hold the magnet 820 with the sensor array 803 while the cement/fluid mixture is injected between the casing 801 and the geological formation 802. The hinge 850 can be spring-loaded, mechanically actuated, or chemically actuated.

For purposes of brevity, the embodiments of FIGS. 4-8 show only one sensor array coupled to the casing. Other embodiments can include multiple sensor arrays located at numerous locations on the casing. These embodiments can have a mixture of different sensor designs (e.g., ex situ, in situ) as well as different types/quantities of sensors in each array.

In operation, NMR is a versatile technique that can make measurements of many different physical and chemical quantities, depending on the pulse sequence used. The pulse sequence can be set in software and changed as for different embodiments. One embodiment includes relaxation and diffusion measurements. These types of measurements can be made in low, grossly inhomogeneous fields with relatively inexpensive hardware.

An NMR measurement depends on the interactions of the $B_1$ and $B_0$ fields through the nuclear spin in a fluid or volume of interest. In identifying the optimum angle ($\alpha$) for a predetermined configuration of the magnet arrangement and common antenna core of the sensor, one may consider the configuration to exist in an arbitrary $R^3$ orthonormal basis set, $\sigma 0$, $\sigma 1$, $\sigma 2$.

The $B_0$ direction at any point dominates the interaction when $B_0 \gg B_1$, which is normally the case for down-hole tools. This implies that only portions perpendicular to the $B_0$ direction will matter for $B_1$. When considering how the $B_1$ field acts this means that only an $R^2$ space will need to be considered. This particular plane will then be called the perpendicular plane, while the direction of $B_0$ is designated as the parallel direction.

The last part of the NMR measurement is to receive a signal from the excited nuclear spins as detected by the sensor array. This occurs according to the principle of reciprocity where the nuclear spins act as mini transmitting coils.

The received data, in contemporary down-hole experiments, reveals two characteristics of magnetization: longitudinal recovery and transverse relaxation. Both of these measurements require the magnetization to be perturbed from its equilibrium state and alignment with the static field. These involve measurements of the magnetization rates to equilibrium from the perturbed states in the directions parallel and perpendicular to the $B_0$ field.

The $T_1$ (spin-lattice) and $T_2$ (spin-spin) relaxation rates can be used as probes of the environment of the spin of interest. From the $T_1$ and $T_2$ distributions, it is possible to receive information such as chemical species, pore size distribution, and extent of contamination of the cement.

Many of the short components can be limited by surface relaxation, where the fluid spins interacting with the ferrite on surfaces in the cement pores undergo a more rapid relaxation process than those in the bulk fluid. These spins may also induce relaxation in neighboring spins, effectively "averaging out" the relaxation times within any given pore. As a result of the interactions, the $T_1$ and $T_2$ of a given component can be related to the surface-to-volume ratio of the pore within which the component resides, with smaller pores inducing faster relaxation.

Figure 9:
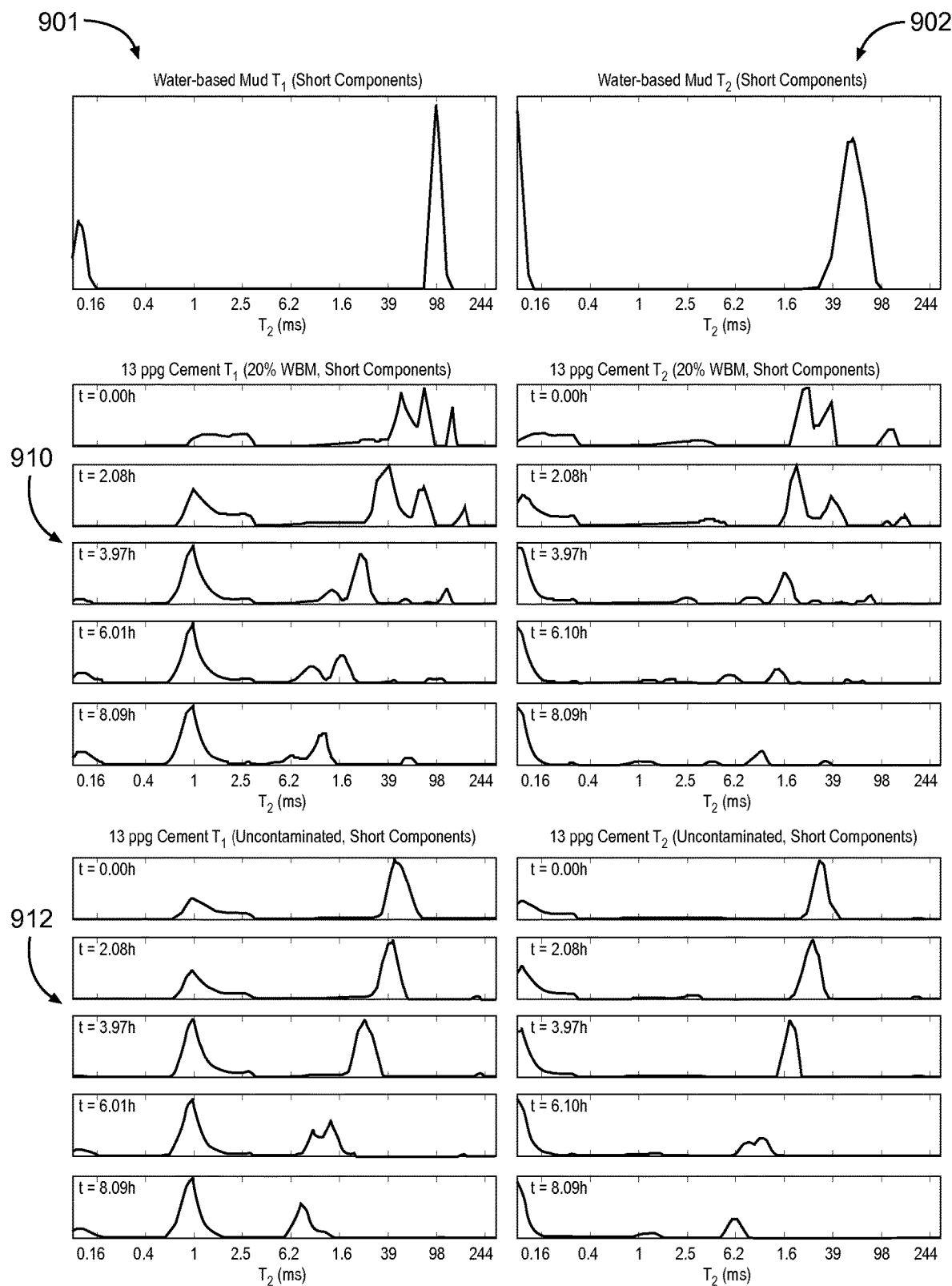
FIG. 9 shows various plots of $T_1$ and $T_2$ spectra of water-based mud, contaminated cement, and uncontaminated cement.

In contrast to the case of oil-based mud, there can be very little long-component signal in uncontaminated or water-based mud contaminated signal, but NMR can still be used to detect contamination by water-based mud from the shorter-component signals as can be seen in FIG. 9.

FIG. 9 illustrates the $T_1$ spectra 901 and the $T_2$ spectra 902 of water-based mud (WBM). This figure further shows 13 parts per gallon (ppg) cement contaminated with 20% WBM 910 and uncontaminated 13 ppg cement 912 as numerous points during the curing process.

FIG. 9 shows that a signal initially at $T_1$=95 ms and $T_2$=56 ms, present only in the water-based mud contaminated spectra 901, shifts significantly with the nearby peak initially at $T_1$=76.8 ms and $T_2$=36.9 ms, indicating that the mud is being incorporated into the structure of the cement. The fact that the anomalous peaks show up almost exclusively near positions where known peaks from uncontaminated cement also appear likely indicates that the WBM is changing the structure of the cement, either by changing the degree of hydration of the components or changing the pore-size distribution.

The signal from these telltale components can tend to go down over time as the free water is incorporated into the cement. This can indicate that the embedded NMR sensors can have an advantage in detecting WBM contamination over the use of wireline or MWD tools. The embedded NMR sensors can further measure water mobility, the pore-size distribution, and the total porosity of the cement. One can then not only identify the degree of the contamination but also its qualitative nature, enabling the determination about the quality of the cement as it cures.

While the above-described embodiments refer to $T_1$-$T_2$ correlation spectra of setting cement, the embedded NMR sensors are not limited to such measurements. In addition to the spatial measurements of $T_2$, measurements of diffusion, or diffusion-$T_2$ correlation spectra, the present embodiments can also measure water mobility and pore size distribution more accurately by running a $T_2$-$T_2$ correlation spectrum.

In a $T_2$-$T_2$ correlation spectrum, spins are allowed to relax via their $T_2$ spin-spin relaxation mechanism for a period of time. The magnetization is stored using an RF pulse and, after some delay, another RF pulse starts the spin decaying under $T_2$ again. During the delay between pulses, spins in an environment decaying under one $T_2$ have time to migrate into a region wherein they would decay under a second $T_2$. This can result in cross-peaks between components that are exchanging spins. The rates of exchange can be determined by repeating the measurement with multiple delays and determining when the cross-peaks begin to appear.

Figure 10:
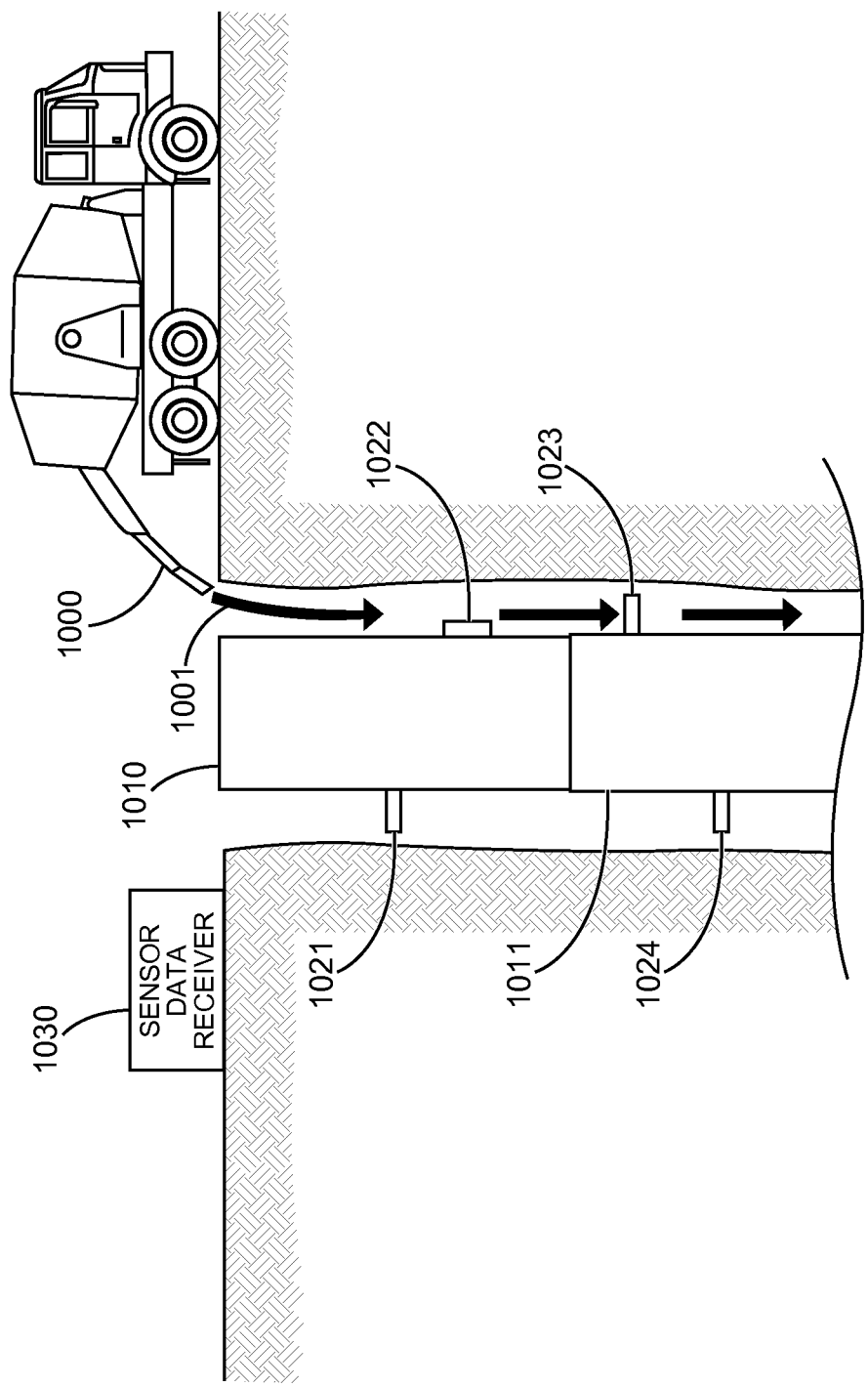
FIG. 10 illustrates an embodiment of a method for creating a system of cement embedded sensors on a casing in a borehole.

FIG. 10 illustrates an embodiment of a system of NMR sensor arrays being used during a method of embedding the sensor arrays in cement. This embodiment is for purposes of illustration only as other methods can be used to embed the system of NMR sensor arrays in cement as it cures.

After the borehole has been drilled, the casings 1010, 1011 are lowered into the borehole. One or more NMR sensor arrays 1021-1024 are peripherally coupled around the outside of the casings 1010, 1011 as previously described. If an expandable sensor array is used, it can be unlatched and extended at this time.

The cement 1001, from a cement source 1000, is injected into the borehole around the sides of the downhole casings 1011, 1011, between the casings 1011, 1011 and the geological formation through which the borehole is drilled. The system of NMR sensor arrays 1021-1024 can provide measured data signals to a sensor data receiver 1030 at the surface to enable the cement composition to be adjusted as it is injected. Similarly, as the cement is setting, the system of NMR sensor arrays 1021-1024 can measure the cement composition and transmit this data to the sensor data receiver 1030.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A sensor system, comprising
   a downhole casing comprising a support arm peripherally coupled to an outside of the casing, and extending from the casing, the support arm comprising a magnetic resonance (MR) sensor spaced apart from the casing along the support arm and embeddable in a cement/fluid mix composition in an annulus external to the downhole casing and operable to monitor the cement/fluid mix composition.

2. The sensor system of claim 1, wherein the MR sensor comprises an in situ sensor.

3. The sensor system of claim 1, wherein the MR sensor comprises an ex situ sensor.

4. The sensor system of claim 1, wherein the MR sensor comprises a plurality of magnets having a hollow core and configured to enable the cement/fluid mix to enter the core when the cement/fluid mix is in a liquid state.

5. The sensor system of claim 1, wherein the MR sensor comprises a spring-loaded, a mechanically actuated, or a chemically actuated assembly configured to move at least a portion of the MR sensor away from the downhole casing in response to being unlatched while remaining coupled to the downhole casing at a hinge.

6. The sensor system of claim 1, wherein the sensor is powered by a battery or battery pack.

7. The sensor system of claim 1, wherein the sensor is powered by an external power source transmitted to the sensor along the outside of the casing via a wired connection or through fiber optic line.

8. The sensor system of claim 1, wherein the MR sensor comprises a plurality of permanent magnets.

9. The sensor system of claim 8, wherein the plurality of permanent magnets each include a hollow core configured to admit entry of the cement/fluid mix when the cement/fluid mix is in a liquid state.

10. The sensor system of claim 1, wherein the MR sensor comprises:
    a plurality of magnets coupled to the support; and
    a plurality of ex situ sensors, each of the ex situ sensors coupled to a respective one of the plurality of magnets.

11. The sensor system of claim 10, wherein each one of the plurality of sensors comprises a coil, wherein the coil is arranged around the exterior of the one of the plurality of magnets to which the sensor is coupled.

12. The sensor system of claim 1, wherein the support arm further comprises a sensor data transmission circuit coupled to the MR sensor and configured to acquire sensor data from the MR sensor and to transmit the sensor data.

13. A borehole data transmission system, comprising:
    a downhole casing;
    a support arm coupled to an exterior of the downhole casing and extending from the casing, the support arm comprising a magnetic resonance (MR) sensor array, each MR sensor of the MR sensor array spaced apart from the casing along the support arm and embeddable in a cement/fluid mix composition in an annulus external to the downhole casing and operable to monitor the cement/fluid mix composition; and
    a sensor data transmission circuit coupled to the MR sensor array and configured to acquire sensor data from the MR sensor array and to transmit the sensor data.

14. The borehole system of claim 13, wherein the MR sensor array comprises a magnet comprising a hollow core.

15. The borehole system of claim 13, wherein the MR sensor is configured to monitor the cement/fluid mix composition while the cement is setting.

16. The borehole system of claim 13, wherein the MR sensor array comprises a plurality of nuclear magnetic resonance (NMR) sensors comprising a magnet and a hollow core and a plurality of NMR sensors comprising a magnet and a coil disposed around the exterior of the magnet.

17. The borehole system of claim 13, further comprising a wireline logging tool to receive the sensor data.

18. The borehole system of claim 13, further comprising a sensor data receiver on a geological formation surface to receive wirelessly receive the sensor data.

19. A method for creating a sensor system, the method comprising:
    drilling a borehole into a geological formation;
    inserting a downhole casing into the borehole, wherein the casing comprises a support arm peripherally coupled to an exterior of the downhole casing and extending from the casing, the support comprising a magnetic resonance (MR) sensor array, each MR sensor of the MR sensor array spaced apart from the casing along the support arm and embeddable in a cement/fluid mix composition in an annulus external to the downhole casing and configured to monitor the cement/fluid mix composition; and
    injecting the cement/fluid mixture between the geological formation and the downhole casing.

20. The method of claim 19, further comprising receiving sensor data from the MR sensor array at a sensor data receiver on a surface of the geological formation.

21. The method of claim 19, further comprising transmitting the sensor data to a sensor data receiver while the cement/fluid mix transitions between a liquid and a solid state.

22. The method of claim 19, further comprising embedding the MR sensor array into the cement/fluid mix composition.

* * * * *